July 11, 1972 W. H. JESSEL, JR., ET AL Plant Pat. 3,233
CHRYSANTHEMUM PLANT
Filed Nov. 12, 1970
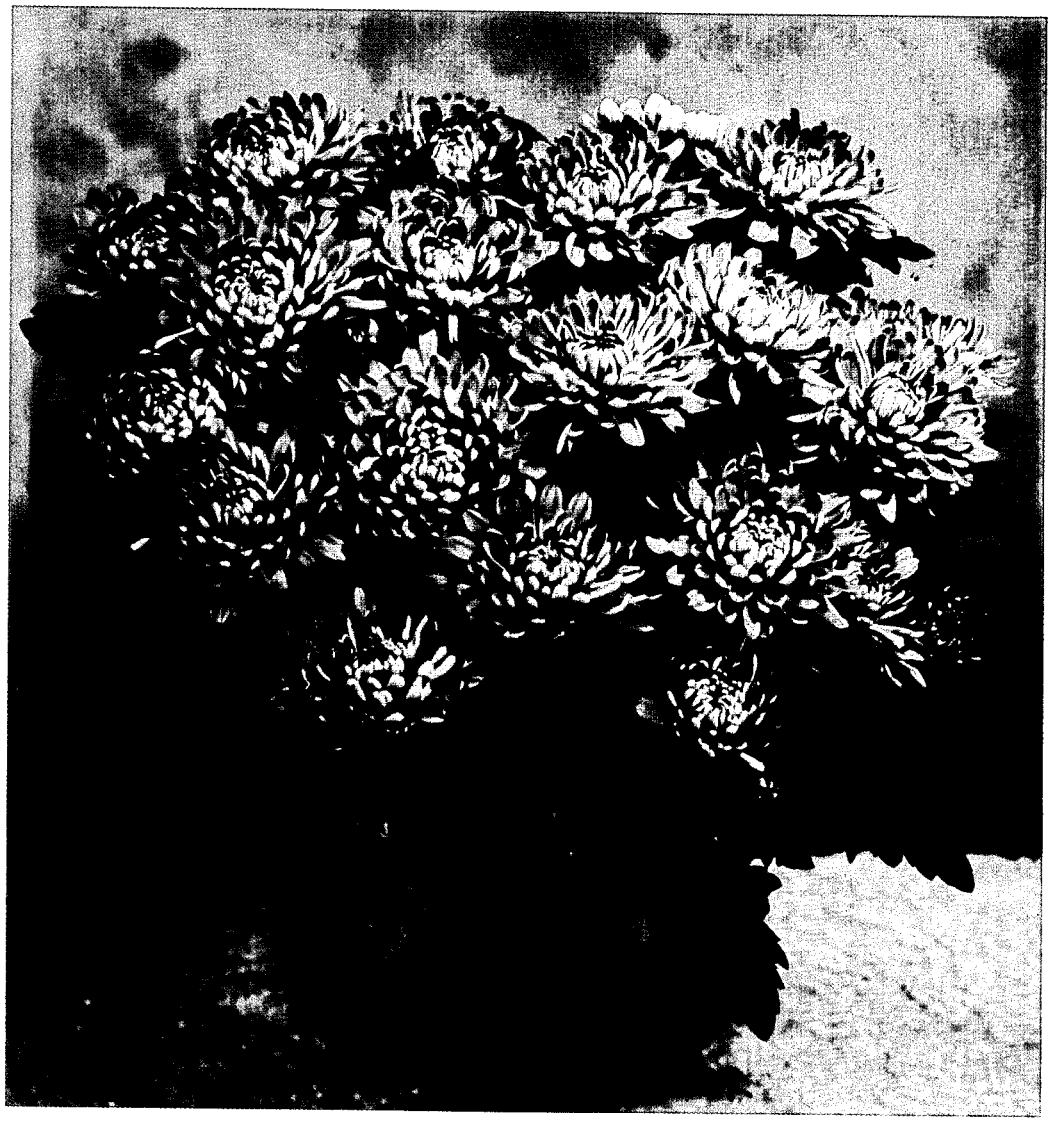
INVENTORS
WALTER H. JESSEL, Jr.
WILLIAM E. DUFFETT
BY Overlin, Maky, Donnelly & Renner
ATTORNEYS

United States Patent Office

Plant Pat. 3,233
Patented July 11, 1972

3,233
CHRYSANTHEMUM PLANT

Walter H. Jessel, Jr., Doylestown, and William E. Duffett, Akron, Ohio, assignors to Yoder Brothers, Inc., Barberton, Ohio

Filed Nov. 12, 1970, Ser. No. 89,153
Int. Cl. A01h *5/00*
U.S. Cl. Plt.—82 1 Claim

The present invention comprises a new and distinct cultivar of chrysanthemum plant which is a sport of the unpatented but commercially well know cultivar Mandalay.

The new cultivar is similar in many respects to Mandalay, having the same characteristics as Mandalay of:

(1) Foliage size.

(2) Foliage shape.

(3) Foliage color.

(4) Similar response during cool temperature periods.

The new cultivar is distinguished from the parent cultivar Mandalay by the following characteristics:

(1) A much deeper red flower color compared to the orange bronze color of Mandalay.

(2) 3 days later in response during high temperature periods.

(3) ¼″ smaller flowers.

(4) Somewhat more incurved flowers.

The new cultivar was selected from a flowering block of the parent cultivar at Yoder Brothers, Inc., in Barberton, Ohio, and when asexually reproduced by cuttings has been found to retain its distinctive characteristics through successive propagations.

The new cultivar when grown in the vicinity of Barberton, Ohio, has a response period of approximately 10 weeks. The response time, blooming period, color and total vigor may vary significantly with varying environmental conditions such as temperature, day length, and light intensity. Suggested flowering in the northern and western United States is from March through November. In the south, from November through June. In Florida, from December through April, and in coastal California, year round.

The accompanying drawing shows the unique characteristics of the new cultivar, the color being as nearly true as possible with color illustrations of this type.

The following data is based on observation of the new cultivar in a greenhouse in Barberton, Ohio. Color references are to the Munsell Color Book, 1963 edition, and comparisons are made where relevant with the parent cultivar Mandalay.

Botanical classification: *Crysanthemum morifolium.*

| | Sparkling Mandalay | Mandalay |
|---|---|---|
| Bloom: | | |
| Size | 3¼″-3¾″ | 3½″-4″. |
| Fully expanded | 4¾″ | 5″. |
| Borne | Terminal on disbudded branches. | Terminal on disbudded branches. |
| Stems | Branches 10″-16″ long | Branches 10″-16″ long. |
| Form | Semi-incurve | Semi-incurve. |
| Permanence | 14-18 days | 14-18 days. |
| Color: | | |
| Center of flower | Greenish yellow, 7.5Y8/8 | Greenish yellow, 7.5Y7/10. |
| Base of petal | Red, 7.5R3/6 over yellow, 5Y8/10 to red bronze, 5R3/8 over yellow, 5Y8.5/10. | Yellow bronze, 10YR7/12 to yellow, 5Y8.5/10. |
| Inside of petals | Do | Do. |
| Reverse of petals | Greenish bronze, 5Y6/ to light streaked bronze, 10R3/6 over light bronze, 2.5Y6/6. | Greenish bronze, 5Y7/8 to light yellow, 5Y8.5/6. |
| Tonality from a distance. | Red | Light bronze. |
| Discoloration | Red bronze | Light yellow bronze. |

Petals:

*Texture.*—Smooth.

*Appearance and form.*—Broadly keeled and tapering to a point.

*Arrangement.*—Composite, whorled on a single receptacle.

*Persistence.*—Resists shatter.

*Fragrance.*—Typical chrysanthemum.

Reproductive organs:

*Stamen, anthers.*—None to 30.

*Pollen.*—None to scant.

*Arrangement.*—Clustered in center of flower, if present.

*Styles.*—Present both ray and disc florets.

*Length.*—Short.

*Ovaries.*—At the base of petal attached to receptacle.

Plant:

*Form.*—Herbaceous.

*Growth.*—Semi-upright.

*Height.*—10″-16″.

*Spread.*—6″-10″.

Foliage:

*Top side.*—Dark green, 10GY2/4.

*Size.*—5¾″ long, 3¾″ wide.

*Quantity.*—Numerous.

*Shape.*—Spatulate lobed.

*Texture.*—Smooth.

*Ribs and veins.*—Prominent.

*Edge.*—Moderately indented.

*Serration.*—Slight.

*Underside.*—Light green, 7.5GY5/4.

*Stipules.*—Rudimentary to prominent.

We claim:

1. A new and distinct cultivar of chrysanthemum characterized particularly as to uniqueness when compared to the parent cultivar Mandalay by a deeper red flower color, three days later in response during high temperature periods, and a somewhat more incurved and ¼″ smaller flower.

No references cited.

ROBERT E. BAGWILL, Primary Examiner

UNITED STATES PATENT OFFICE

CERTIFICATE OF CORRECTION

Patent No. PP-3,233 Dated July 11, 1972

Inventor(s) Walter H. Jessel, Jr. and William E. Duffett

It is certified that error appears in the above-identified patent and that said Letters Patent are hereby corrected as shown below:

In column 2, line 11, opposite "Base of petal", under "Sparkling Mandalay", the description should read "Red, 7.5R3/6 over yellow, 5Y8.5/10 ..." ; line 14, opposite "Reverse of petal", under "Sparkling Mandalay", the description should read "Greenish bronze, 5Y6/8 ..." .

In column 1, line 13, "know" should be --known--.

Signed and sealed this 2nd day of October 1973.

(SEAL)
Attest:

EDWARD M.FLETCHER,JR.
Attesting Officer

RENE D. TEGTMEYER
Acting Commissioner of Patents

USCOMM-DC 60376-P69
☆ U.S. GOVERNMENT PRINTING OFFICE : 1969 O—366-334